US007740574B2

(12) United States Patent
Pilla et al.

(10) Patent No.: US 7,740,574 B2
(45) Date of Patent: **\*Jun. 22, 2010**

(54) ELECTROMAGNETIC TREATMENT INDUCTION APPARATUS AND METHOD FOR USING SAME

(75) Inventors: Arthur A. Pilla, Oakland, NJ (US); Andre' DiMino, Woodcliff Lake, NJ (US); Iyer Viswanathan, Santa Clara, CA (US)

(73) Assignee: Ivivi Technologies, Inc., Montvale, NJ (US)

( \* ) Notice: Subject to any disclaimer, the term of this patent is extended or adjusted under 35 U.S.C. 154(b) by 1141 days.

This patent is subject to a terminal disclaimer.

(21) Appl. No.: 11/114,666

(22) Filed: Apr. 26, 2005

(65) Prior Publication Data

US 2005/0288744 A1    Dec. 29, 2005

Related U.S. Application Data

(60) Provisional application No. 60/564,887, filed on Apr. 26, 2004.

(51) Int. Cl.
*A61N 1/00* (2006.01)

(52) U.S. Cl. ........................................................ 600/13

(58) Field of Classification Search ................ 600/9–15
See application file for complete search history.

(56) References Cited

U.S. PATENT DOCUMENTS

2003/0171640 A1\* 9/2003 Canedo .......................... 600/9
2005/0065394 A1\* 3/2005 Spiegel .......................... 600/9

\* cited by examiner

*Primary Examiner*—Charles A Marmor, II
*Assistant Examiner*—Christine D Hopkins
(74) *Attorney, Agent, or Firm*—Len Taylor, Esq.

(57) ABSTRACT

A lightweight inductive apparatus is integrated into at least one therapeutic device (Step 101). Miniaturized circuitry containing logic for a mathematical model having at least one waveform parameter used to configure at least one waveform to be coupled to a target pathway structure such as molecules, cells, tissues, and organs, is attached to the coil by at least one wire (Step 102). The configured waveform satisfies a SNR or Power SNR model so that for a given and known target pathway structure it is possible to choose at least one waveform parameter so that a waveform is detectable in the target pathway structure above its background activity (Step 103). A repetitive electromagnetic signal can be generated for example inductively, from said configured at least one waveform (Step 104). The electromagnetic signal is coupled to a target pathway structure by output of the inductive apparatus (Step 105).

27 Claims, 10 Drawing Sheets

ELECTROMAGNETIC TREATMENT INDUCTION APPARATUS AND METHOD FOR USING SAME

This application claims the benefit of U.S. Provisional Application 60/564,887 filed Apr. 26, 2004.

BACKGROUND OF THE INVENTION

1. Field of the Invention

This invention pertains generally to an electromagnetic treatment induction apparatus and a method for using same to achieve modification of cellular and tissue growth, repair, maintenance, and general behavior by application of encoded electromagnetic information. More particularly this invention relates to the application of surgically non-invasive coupling of highly specific electromagnetic signal patterns to any number of body parts. In particular, an embodiment according to the present invention pertains to using an induction means such as a coil to deliver pulsing electromagnetic fields ("PEMF") to enhance living tissue growth and repair in conjunction with devices such as supports, wraps, beds, and wheelchairs, and in conjunction with other therapeutic and wellness physical modalities, such as ultrasound, negative or positive pressure, heat, cold, massage.

2. Discussion of Related Art

It is now well established that application of weak non-thermal electromagnetic fields ("EMF") can result in physiologically meaningful in vivo and in vitro bioeffects.

EMF has been used in applications of bone repair and bone healing. Waveforms comprising low frequency components and low power are currently used in orthopedic clinics. Origins of using bone repair signals began by considering that an electrical pathway may constitute a means through which bone can adaptively respond to EMF signals. A linear physicochemical approach employing an electrochemical model of a cell membrane predicted a range of EMF waveform patterns for which bioeffects might be expected. Since a cell membrane was a likely EMF target, it became necessary to find a range of waveform parameters for which an induced electric field could couple electrochemically at the cellular surface, such as voltage-dependent kinetics. Extension of this linear model also involved Lorentz force analysis.

A pulsed radio frequency ("PRF") signal derived from a 27.12 MHz continuous sine wave used for deep tissue healing is known in the prior art of diathermy. A pulsed successor of the diathermy signal was originally reported as an electromagnetic field capable of eliciting a non-thermal biological effect in the treatment of infections. PRF therapeutic applications have been reported for reduction of post-traumatic and post-operative pain and edema in soft tissues, wound healing, burn treatment and nerve regeneration. Application of EMF for the resolution of traumatic edema has become increasingly used in recent years. Results to date using PRF in animal and clinical studies suggest that edema may be measurably reduced from such electromagnetic stimulus.

Prior art considerations of EMF dosimetry have not taken into account dielectric properties of tissue structure as opposed to the properties of isolated cells.

In recent years, clinical use of non-invasive PRF at radio frequencies comprised using pulsed bursts of a 27.12 MHz sinusoidal wave, wherein each pulse burst comprises a width of sixty-five microseconds, having approximately 1,700 sinusoidal cycles per burst, and various burst repetition rates. This limited frequency components that could couple to relevant dielectric pathways in cells and tissue.

Time-varying electromagnetic fields, comprising rectangular waveforms such as pulsing electromagnetic fields, and sinusoidal waveforms such as pulsed radio frequency fields ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. Various studies conclude that upregulation of growth factor production may be a common denominator in the tissue level mechanisms underlying electromagnetic stimulation. When using specific inhibitors, EMF can act through a calmodulin-dependent pathway. It has been previously reported that specific PEMF and PRF signals, as well as weak static magnetic fields, modulate $Ca^{2+}$ binding to CaM in a cell-free enzyme preparation. Additionally, upregulation of mRNA for BMP2 and BMP4 with PEMF in osteoblast cultures and upregulation of TGF-β1 in bone and cartilage with PEMF have been demonstrated.

However, prior art in this field does not use an induction apparatus that is lightweight, portable, disposable, implantable, and configured with, integrated into, or attached to at least one of garments, fashion accessories, footware, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices, ultrasound, heat, cold, massage, and exercise.

Therefore, a need exists for an electromagnetic treatment induction apparatus and a method for using same that is lightweight, portable, implantable, and can be disposable. A further need exists for an electromagnetic treatment induction apparatus and method that can be used more effectively with miniaturized circuitry that optimally configures electromagnetic waveforms to be inductively coupled with plant, animal, and human tissue, organs, cells, and molecules for therapeutic treatment.

SUMMARY OF THE INVENTION

An electromagnetic treatment induction apparatus and a method for using same for therapeutic treatment of living tissues and cells by inductively coupling optimally configured waveforms to alter the living tissues and cells' interaction with their electromagnetic environment.

According to an embodiment of the present invention, by treating a selectable body region with a flux path comprising a succession of EMF pulses having a minimum width characteristic of at least about 0.01 microseconds in a pulse burst envelope having between about 1 and about 100,000 pulses per burst, in which a voltage amplitude envelope of said pulse burst is defined by a randomly varying parameter in which instantaneous minimum amplitude thereof is not smaller than the maximum amplitude thereof by a factor of one ten-thousandth. The pulse burst repetition rate can vary from about 0.01 to about 10,000 Hz. A mathematically definable parameter can also be employed to define an amplitude envelope of said pulse bursts.

By increasing a range of frequency components transmitted to relevant cellular pathways, access to a large range of biophysical phenomena applicable to known healing mechanisms, including enhanced enzyme activity and growth factor and cytokine release, is advantageously achieved.

According to an embodiment of the present invention, by applying a random, or other high spectral density envelope, to a pulse burst envelope of mono- or bi-polar rectangular or sinusoidal pulses which induce peak electric fields between $10^{-6}$ and 10 volts per centimeter (V/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby modulating angiogenesis and neovascularization.

By advantageously applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

A preferred embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 µV/cm to about 100 mV/cm. Each signal burst envelope may be a random function providing a means to accommodate different electromagnetic characteristics of healing tissue. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to provide an electromagnetic method of treatment of living cells and tissues comprising a broad-band, high spectral density electromagnetic field.

It is a further object of the present invention to provide an electromagnetic method of treatment of living cells and tissues comprising amplitude modulation of a pulse burst envelope of an electromagnetic signal that will induce coupling with a maximum number of relevant EMF-sensitive pathways in cells or tissues.

It is an object of the present invention to configure a power spectrum of a waveform by mathematical simulation by using signal to noise ratio ("SNR") analysis to configure a waveform optimized to modulate angiogensis and neovascualarization then coupling the configured waveform using a generating device such as ultra lightweight wire coils that are powered by a waveform configuration device such as miniaturized electronic circuitry.

It is an object of the present invention to provide lightweight flexible coils, that can be placed in at least one of garments, fashion accessories, footware, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices and dressings to deliver the optimum dose of non-invasive pulsed electromagnetic treatment configured as shown above, for enhanced repair and growth of living tissue in animals, humans and plants.

It is another object of the present invention to provide multiple coils, delivering a waveform configured by SNR/Power analysis of a target pathway, to increase area of treatment coverage.

It is another object of the present invention to provide multiple coils that are simultaneously driven or that are sequentially driven such as multiplexed, with the same or different optimally configured waveforms as shown above.

It is a further object of the present invention to provide flexible, lightweight coils that focus the EMF signal to the affected tissue by incorporating the coils, delivering a waveform configured by SNR/Power analysis of a target pathway, into ergonomic support garments.

It is yet a further object of the present invention to utilize conductive thread to create daily wear, and exercise and sports garments having integrated coils, delivering a waveform configured by SNR/Power analysis of a target pathway, positioned in proximity to an anatomical target.

It is yet a further object of the present invention to utilize lightweight flexible coils or conductive thread to deliver the EMF signal to affected tissue by incorporating such coils or conductive threads as an integral part of various types of bandages, such as, compression, elastic, cold compress and hot compress and delivering a waveform configured by SNR/Power analysis of a target pathway.

It is another object of the present invention to employ several coils, delivering a waveform configured by SNR/Power analysis of a target pathway, to increase EMF coverage area.

It is another object of the present invention to construct a coil, delivering a waveform configured by SNR/Power analysis of a target pathway, using conductive thread.

It is another object of the present invention to construct a coil, delivering a waveform configured by SNR/Power analysis of a target pathway, using fine flexible conductive wire.

It is another object of the present invention to supply the same or different waveforms configured by SNR/Power analysis of a target pathway, simultaneously or sequentially to single or multiple coils.

It is yet a further object of the present invention to incorporate at least one coil in a surgical wound dressing to apply an enhanced EMF signal non-invasively and non-surgically, the surgical wound dressing to be used in combination with standard wound treatment.

It is another object of the present invention to construct the coils delivering a waveform configured by SNR/Power analysis of a target pathway, for easy attachment and detachment to dressings, garments and supports by using an attachment means such as Velcro, an adhesive and any other such temporary attachment means.

It is another object of the present invention to provide coils delivering a waveform configured by SNR/Power analysis of a target pathway, that are integrated with therapeutic beds, therapeutic chairs, and wheelchairs.

It is another object of the present invention to provide coils delivering a waveform configured by SNR/Power analysis of a target pathway, that are integrated with various therapy surfaces, such as pressure relieving, inflatable, fluid, viscoelastic and air fluidized bed and other support surfaces.

It is another object of the present invention to provide coils delivering a waveform configured by SNR/Power analysis of a target pathway that are integrated with therapeutic seat cushions such as inflatable, fluidized, foam cushions.

It is another object of the present invention to provide coils delivering a waveform configured by SNR/Power analysis of a target pathway, that are integrated with at least one of therapeutic mattress overlays, sheets, blankets, pillows, pillow cases, and therapeutic devices that can apply steady or intermittent pressure such as air clearance vests.

It is another object of the present invention to provide for the inclusion of a flux path to any therapeutic surface, structure, or device to enhance the effectiveness of such therapeutic surfaces, structures or devices by delivering a waveform configured by SNR/Power analysis of a target pathway.

It is another object of the present invention to incorporate coils delivering a waveform configured by SNR/Power analysis of a target pathway, in footware such as shoes.

It is another object of the present invention to integrate at least one coil delivering a waveform configured by SNR/Power analysis of a target pathway, with a therapeutic surface, structure or device to enhance the effectiveness of such therapeutic surface, structure or device.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

Preferred embodiments of the present invention will be described below in more detail, with reference to the accompanying drawings.

DETAILED DESCRIPTION

Figure 1:
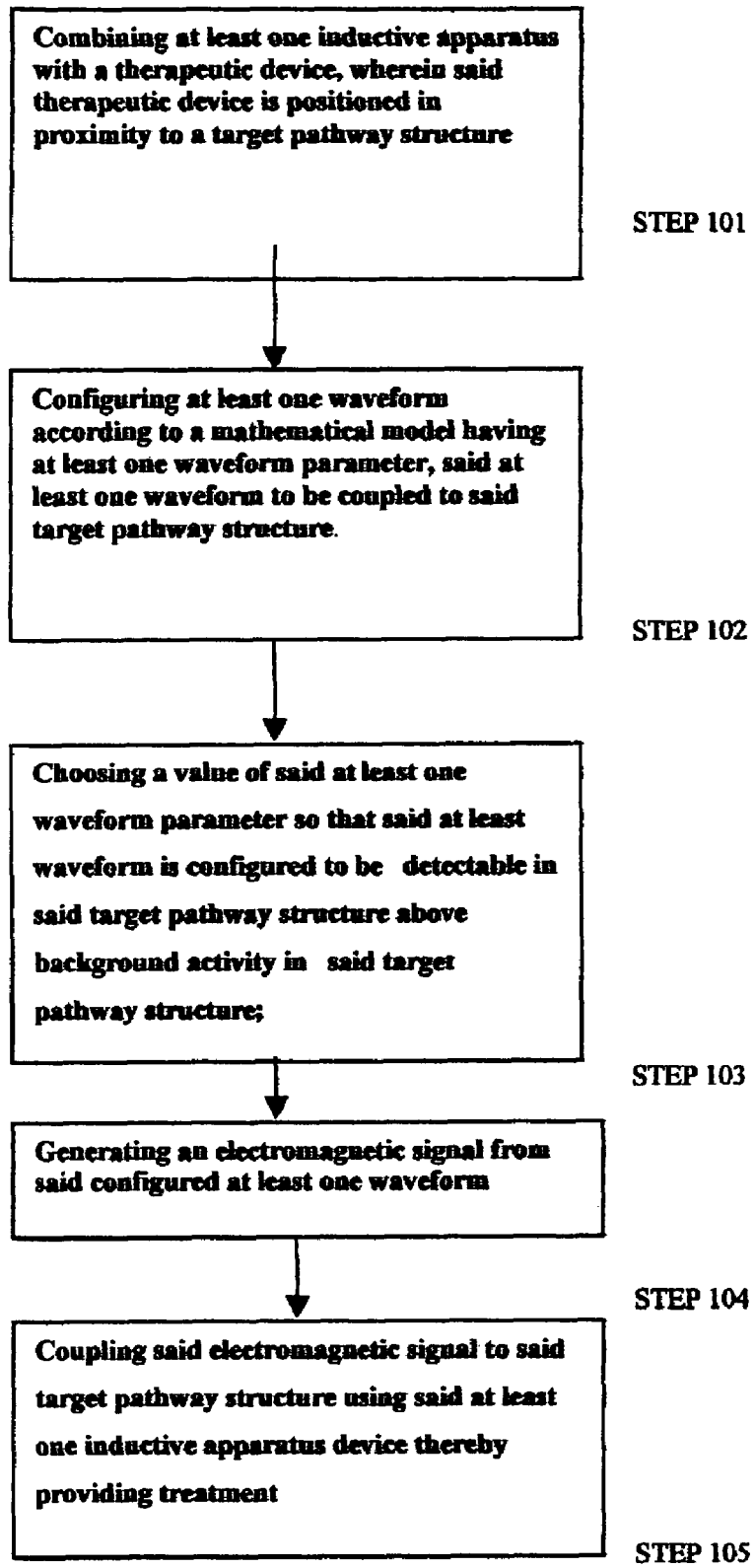
FIG. 1 is a flow diagram of a method for using an electromagnetic treatment inductive apparatus according to an embodiment of the present invention.

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}-1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to wound repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, $[Ca^{2+}]=2.5$ $\mu M$, $K_D=30$ $\mu M$, $[Ca^{2+}CaM]=K_D([Ca^{2+}]+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kT\,Re[Z_M(x,\omega)]$$

where $Z_M(x, \omega)$ is electrical impedance of a target pathway structure, x is a dimension of a target pathway structure and Re denotes a real part of impedance of a target pathway structure. $Z_M(x, \omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4kT\,Re[Z_M(x,\omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known healing mechanisms is accessible. According to an embodiment of the present invention applying a random, or other high spectral density envelope, to a pulse burst envelope of mono- or bipolar rectangular or sinusoidal pulses inducing peak electric fields between about $10^{-6}$ and about 100 V/cm, produces a greater effect on biological healing processes applicable to.- both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 1, wherein FIG. 1 is a flow diagram of a method of using an inductive apparatus to deliver electromagnetic signals to target pathway structures such as such as molecules, cells, tissues, and organs of plants, animals, and humans for therapeutic and prophylactic purposes according to an embodiment of the present invention. A lightweight inductive apparatus is integrated into at least one therapeutic device that will be used for treatment, however the inductive apparatus can also be attached to at least one therapeutic device (Step 101). Miniaturized circuitry containing logic for a mathematical model having at least one waveform parameter used to configure at least one waveform to be coupled to a target pathway structure such as molecules, cells, tissues, and organs, is attached to the coil by at least one wire (Step 102). However, the attachment can also be wireless. The configured waveform satisfies a SNR or Power SNR model so that for a given and known target pathway structure it is possible to choose at least one waveform parameter so that a waveform is detectable in the target pathway structure above its background activity (Step 103) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 104). A repetitive electromagnetic signal can be generated for example inductively, from said configured at least one waveform (Step 105). The repetitive electromagnetic signal can also be generated conductively. The electromagnetic signal is coupled to a target pathway structure such as molecules, cells, tissues, and organs by output of the inductive apparatus integrated into the support (Step 106).

Figure 2:
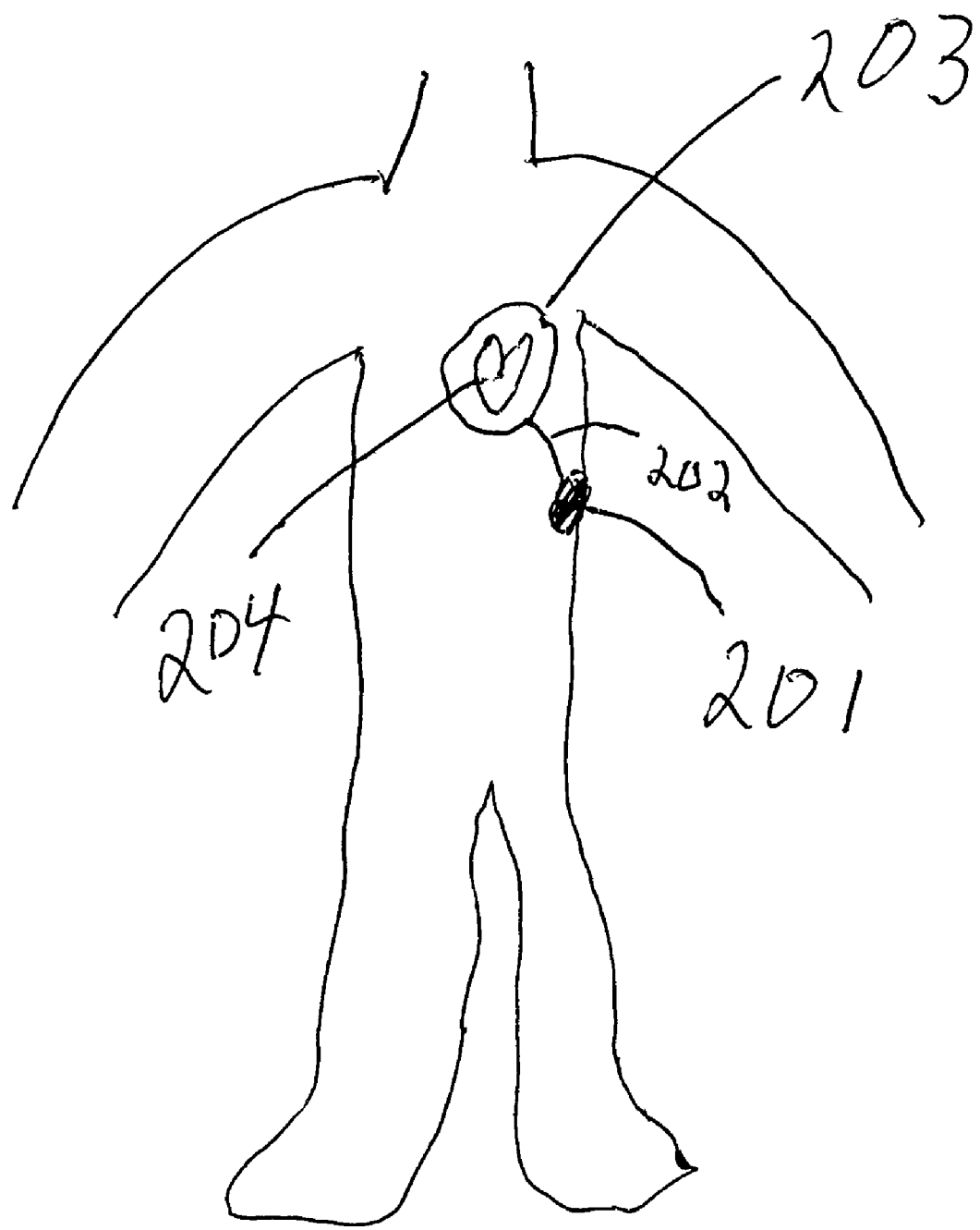
FIG. 2 is a view of control circuitry according to a preferred embodiment of the present invention.

FIG. 2 illustrates a preferred embodiment of an apparatus according to the present invention. A miniature control circuit 201 is coupled to an end of at least one connector 202 such as wire. The opposite end of the at least one connector is coupled to a generating device such as a pair of electrical coils 203. The generating device is constructed to have electrical properties that optimize generation of electromagnetic signals from waveforms configured to satisfy at least one of a SNR model, a Power SNR model, and any other mathematical model used for waveform configuration. The miniature control circuit 201 is constructed in a manner that applies a mathematical model that is used to configure waveforms. The configured waveforms have to satisfy a SNR or Power SNR model so that for a given and known target pathway structure, it is possible to choose waveform parameters that satisfy SNR or Power SNR so that a waveform is detectable in the target pathway structure above its background activity. A preferred embodiment according to the present invention applies a mathematical model to induce a time-varying magnetic field and a time-varying electric field in a target pathway structure such as molecules, cells, tissues, and organs, comprising about 10 to about 100 msec bursts of about 1 to about 100 microsecond rectangular pulses repeating at about 0.1 to about 10 pulses per second. Peak amplitude of the induced electric field is between about 1 UV/cm and about 100 mV/cm, varied according to a modified 1/f function where f=frequency. A waveform configured using a preferred embodiment according to the present invention may be applied to a target pathway structure such as molecules, cells, tissues, and organs for a preferred total exposure time of under 1 minute to 240 minutes daily. However other exposure times can be used. Waveforms configured by the miniature control circuit 201 are directed to a generating device 203 such as electrical coils via connector 202. The generating device 203 delivers a pulsing magnetic field configured according to a mathematical model, that can be used to provide treatment to a target pathway structure such as a heart in a chest 204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the heart in a chest 204 by a positioning device. Coupling a pulsing magnetic field to a angiogenesis and neovascularization target pathway structure such as ions and ligands, therapeutically and prophylactically reduces inflammation thereby reducing pain and promotes healing. When electrical coils are used as the generating device 203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 203 can also be applied using electrostatic coupling wherein an air gap exists between a generating device 203 such as an electrode and a target pathway structure such as molecules, cells, tissues, and organs. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's angiogenesis and neovascularization can be maintained and enhanced.

Figure 3:
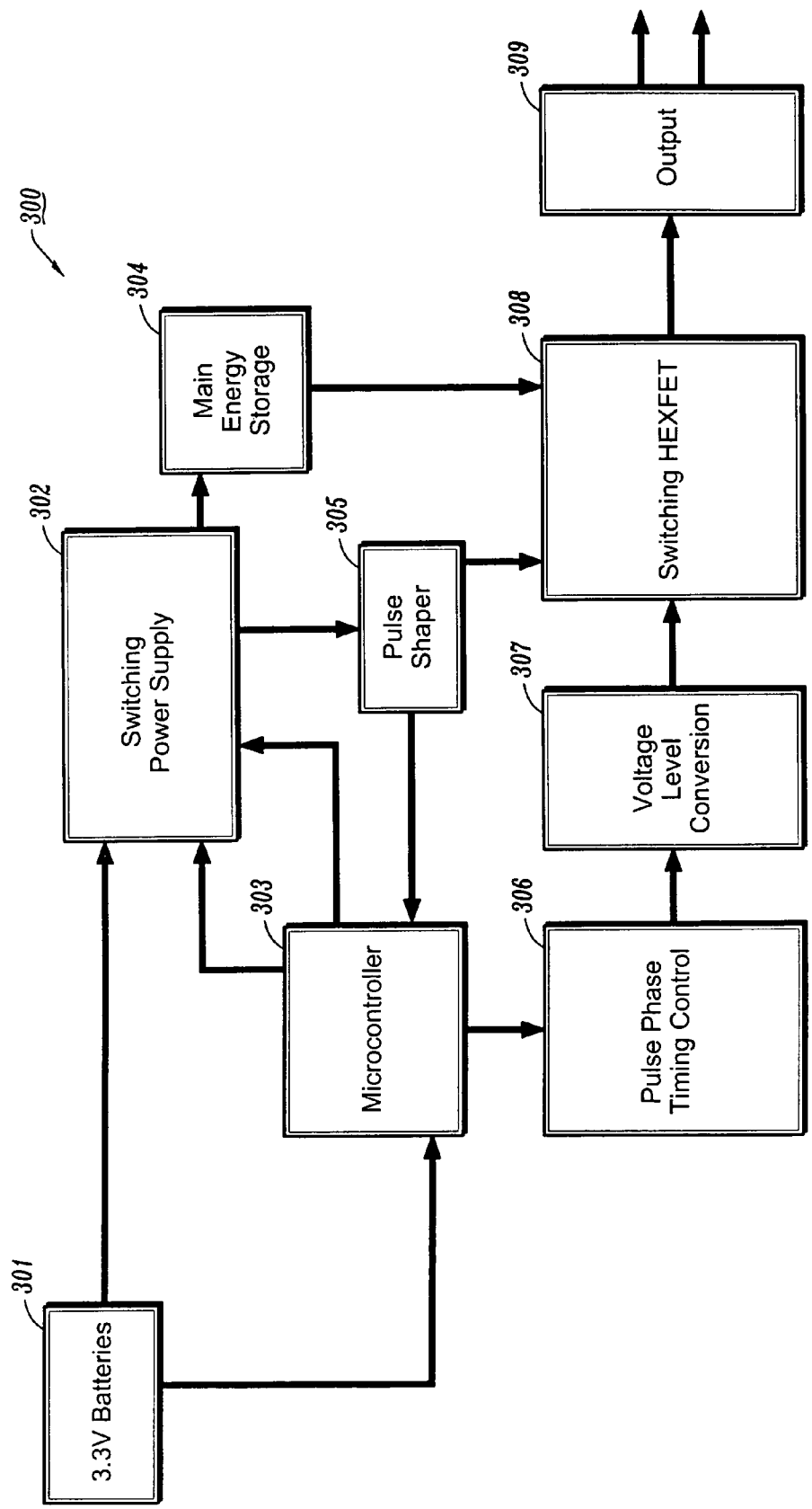
FIG. 3 is a block diagram of miniaturized circuitry according to a preferred embodiment of the present invention.

FIG. 3 depicts a block diagram of a preferred embodiment according to the present invention of a miniature control circuit 300. The miniature control circuit 300 produces waveforms that drive a generating device such as wire coils described above in FIG. 2. The miniature control circuit can be activated by any activation means such as an on/off switch. The miniature control circuit 300 has a power source such as a lithium battery 301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 302 controls voltage to a micro-controller 303. A preferred embodiment of the micro-controller 303 uses an 8 bit 4 MHz micro-controller 303 but other bit MHz combination micro-controllers may be used. The switching power supply 302 also delivers current to storage capacitors 304. A preferred embodiment of the present invention uses storage capacitors having a 220 uF output but other outputs can be used. The storage capacitors 304 allow high frequency pulses to be delivered to a coupling device such as inductors (Not Shown). The micro-controller 303 also controls a pulse shaper 305 and a pulse phase timing control 306. The pulse shaper 305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 308 controls an induced field delivered to a target pathway structure. A switching Hexfet 308 allows pulses of randomized amplitude to be delivered to output 309 that routes a waveform to at least one coupling device such as an inductor. The micro-controller 303 can also control total exposure time of a single treatment of a target pathway structure such as a molecule, cell, tissue, and organ. The miniature control circuit 300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Figure 4:
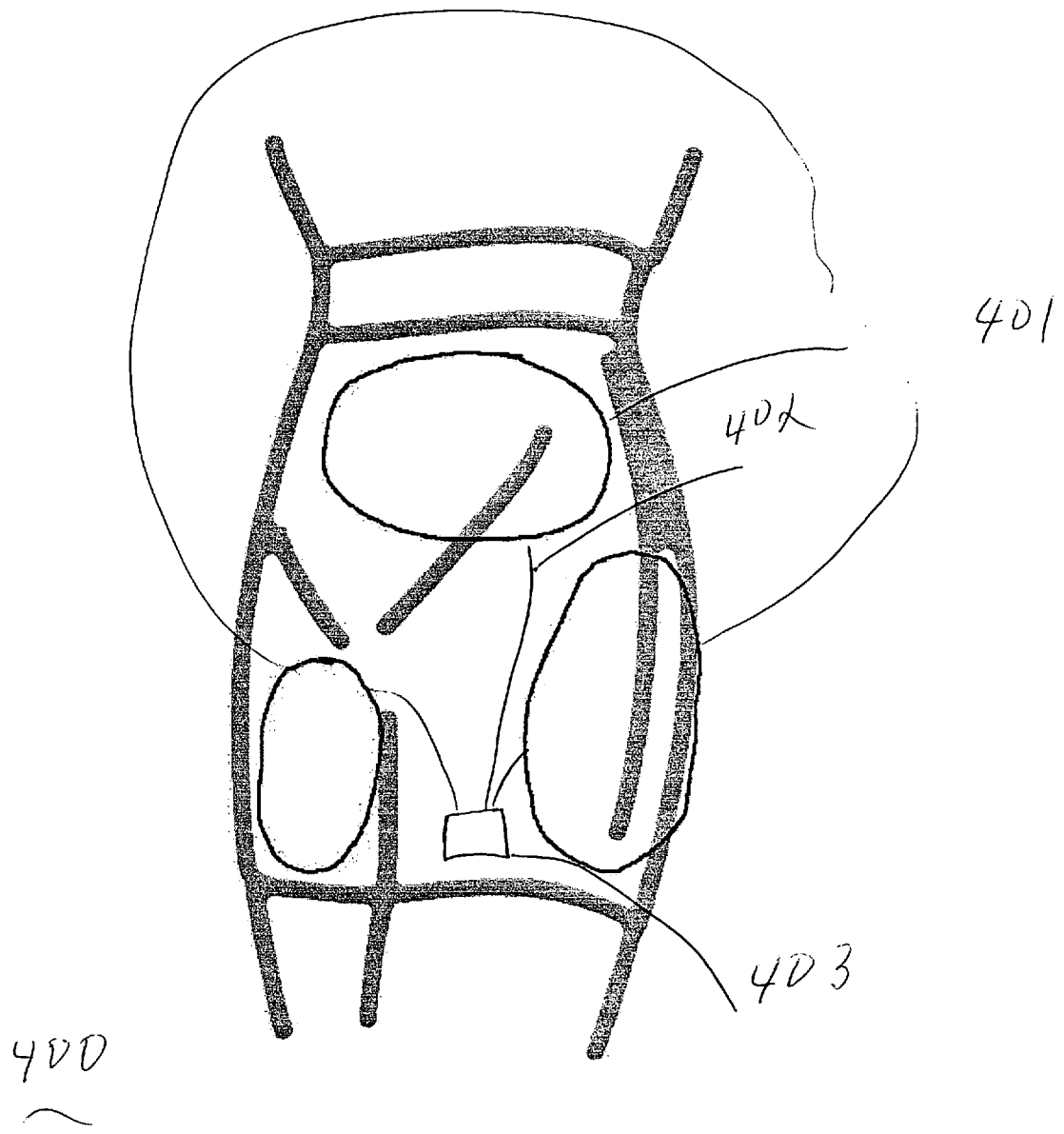
FIG. 4 depicts an electromagnetic treatment inductive apparatus integrated into a hip, thigh, and lower back support garment according to a preferred embodiment of the present invention.

Referring to FIG. 4 an embodiment according to the present invention of an electromagnetic treatment inductive apparatus integrated into hip, thigh, and lower back support garment 400 is illustrated. Several lightweight flexible coils 401 are integrated into the support garment. The lightweight flexible coils can be constructed from fine flexible conductive wire, conductive thread, and any other flexible conductive material. The flexible coils are connected to at least one end of at least one wire 402. However the flexible coils can also be configured to be directly connected to circuitry 403 or wireless. Lightweight miniaturized circuitry 403 that configures waveforms according to an embodiment of the present invention, is attached to at least one other end of said at least on wire. When activated the lightweight miniaturized circuitry 403 configures waveforms that are directed to the flexible coils (401) to create PEMF signals that are coupled to a target pathway structure.

Figure 5:
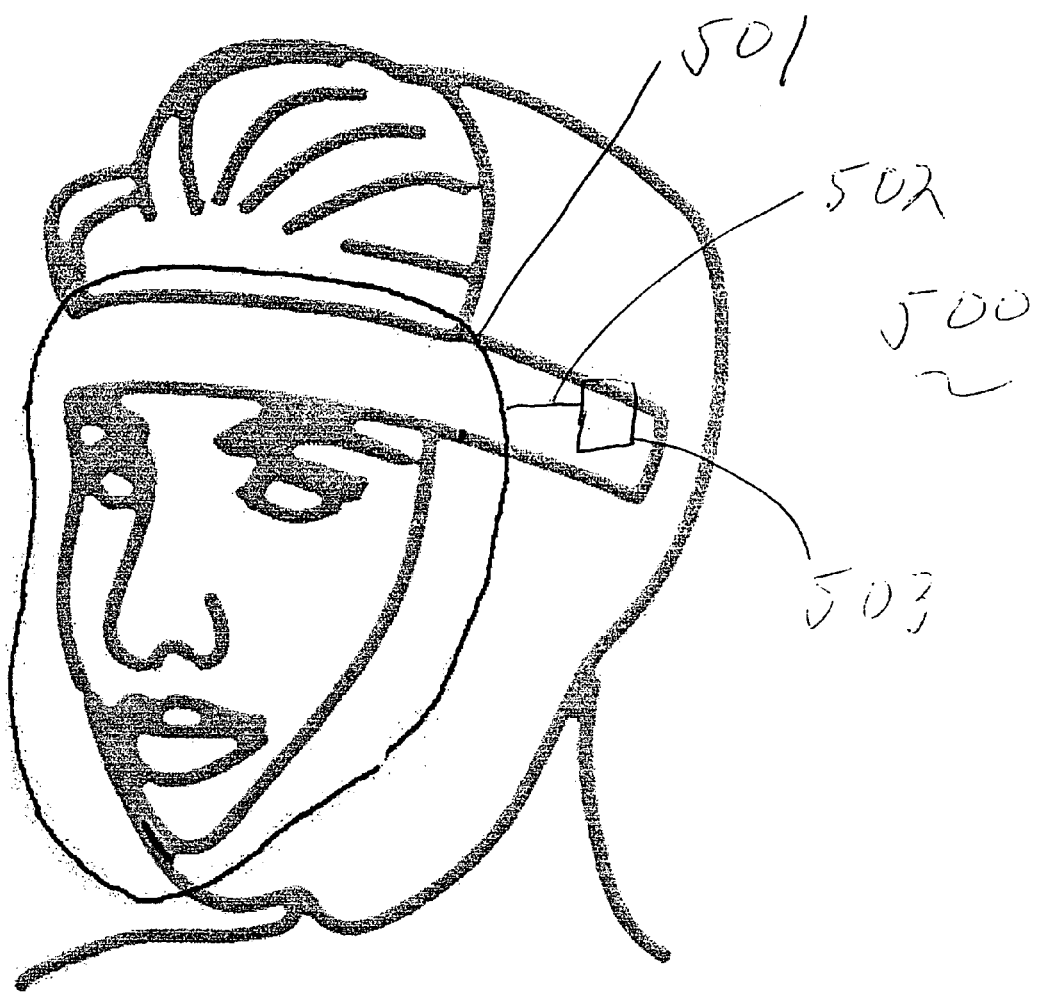
FIG. 5 depicts an electromagnetic treatment inductive apparatus integrated into a head and face support garment according to a preferred embodiment of the present invention.

Referring to FIG. 5 an embodiment according to the present invention of an electromagnetic treatment inductive apparatus integrated into a head and face support garment 500 is illustrated. Several lightweight flexible coils 501 are integrated into the support garment. The lightweight flexible coils can be constructed from fine flexible conductive wire, conductive thread, and any other flexible conductive material. The flexible coils are connected to at least one end of at least one wire 502. However, the flexible coils can also be configured to be directly connected to circuitry 503 or wireless. Lightweight miniaturized circuitry 503 that configures waveforms, according to an embodiment of the present invention, is attached to at least one other end of said at least on wire. When activated the lightweight miniaturized circuitry 503 configures waveforms that are directed to the flexible coils (501) to create PEMF signals that are coupled to a target pathway structure.

Figure 6:
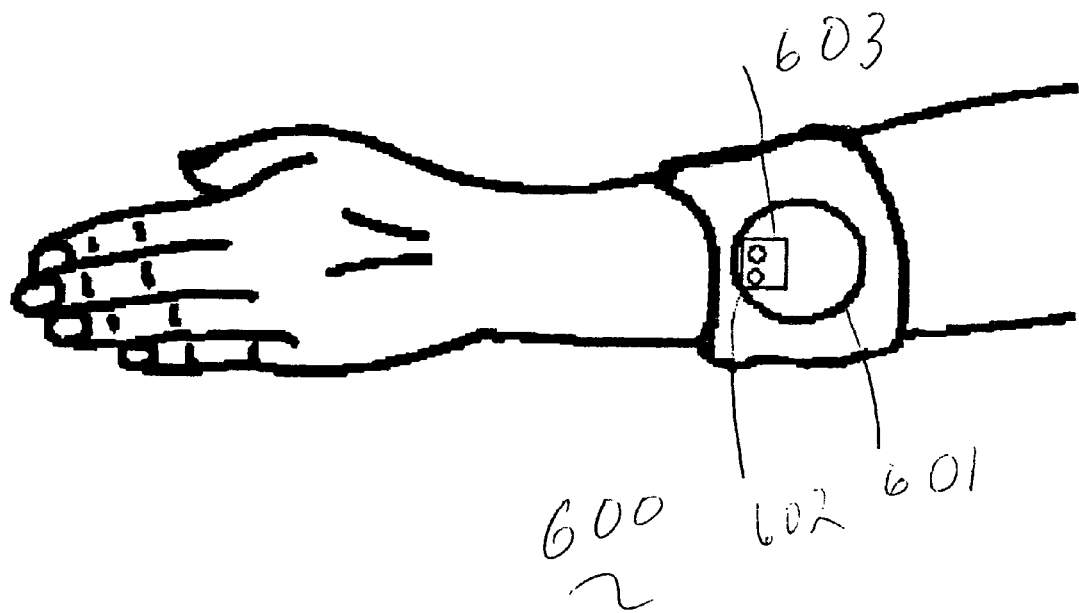
FIG. 6 depicts an electromagnetic treatment inductive apparatus integrated into a surgical dressing on a human forearm according to a preferred embodiment of the present invention.

Referring to FIG. 6 an embodiment according to the present invention of an electromagnetic treatment inductive apparatus integrated into surgical dressing applied to a human forearm 600 is illustrated. Several lightweight flexible coils 601 are integrated into the dressing. The lightweight flexible coils can be constructed from fine flexible conductive wire, conductive thread, and any other flexible conductive material. The flexible coils are connected to at least one end of at least one wire 602. However, the flexible coils can also be configured to be directly connected to circuitry 603 or wireless. Lightweight miniaturized circuitry 603 that configures waveforms according to an embodiment of the present invention, is attached to at least one other end of said at least one wire. When activated the lightweight miniaturized circuitry 603 configures waveforms that are directed to the flexible coils (601) to create PEMF signals that are coupled to a target pathway structure.

Figure 7:
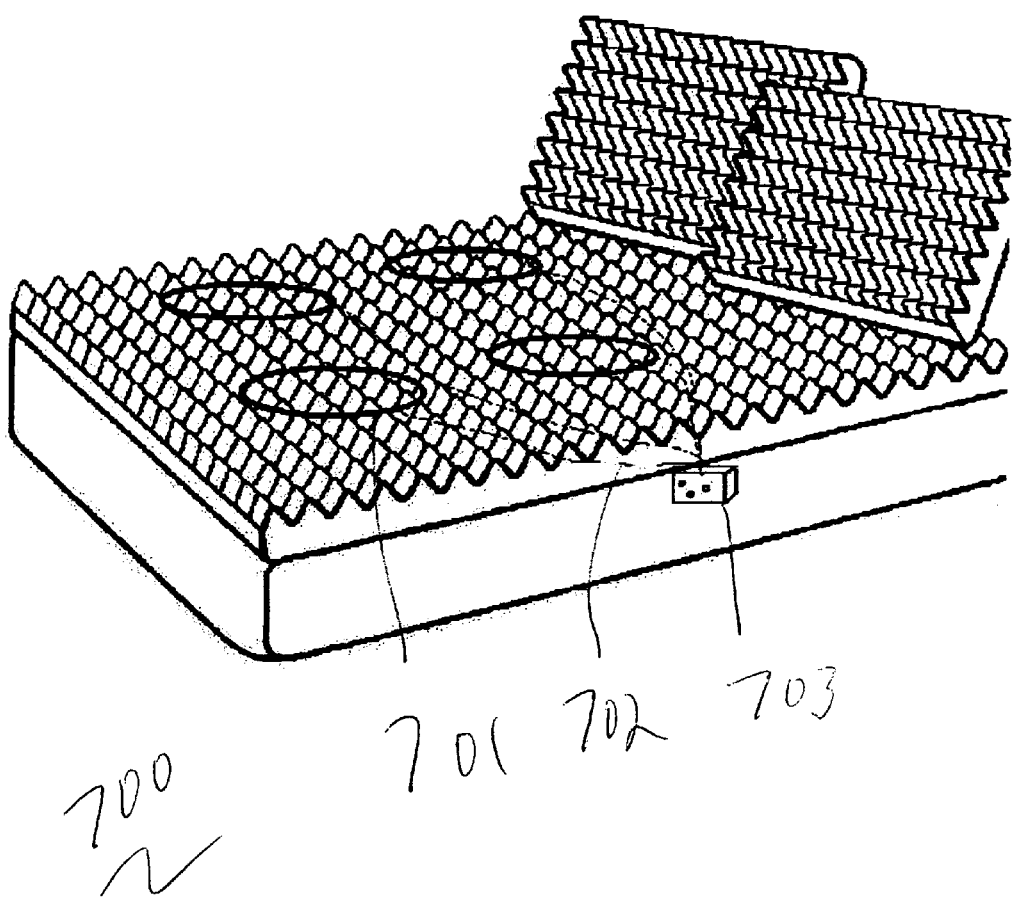
FIG. 7 depicts an electromagnetic treatment inductive apparatus integrated into a mattress pad according to a preferred embodiment of the present invention.

Referring to FIG. 7 an embodiment according to the present invention of an electromagnetic treatment inductive apparatus integrated into a mattress pad 700 is illustrated. Several lightweight flexible coils 701 are integrated into the mattress pad. The lightweight flexible coils can be constructed from fine flexible conductive wire, conductive thread, and any other flexible conductive material. The flexible coils are connected to at least one end of at least one wire 702. However, the flexible coils can also be configured to be directly connected to circuitry 703 or wireless. Lightweight miniaturized circuitry 703 that configures waveforms according to an embodiment of the present invention, is attached to at least one other end of said at least on wire. When activated the lightweight miniaturized circuitry 703 configures waveforms that are directed to the flexible coils (701) to create PEMF signals that are coupled to a target pathway structure.

Figure 8:
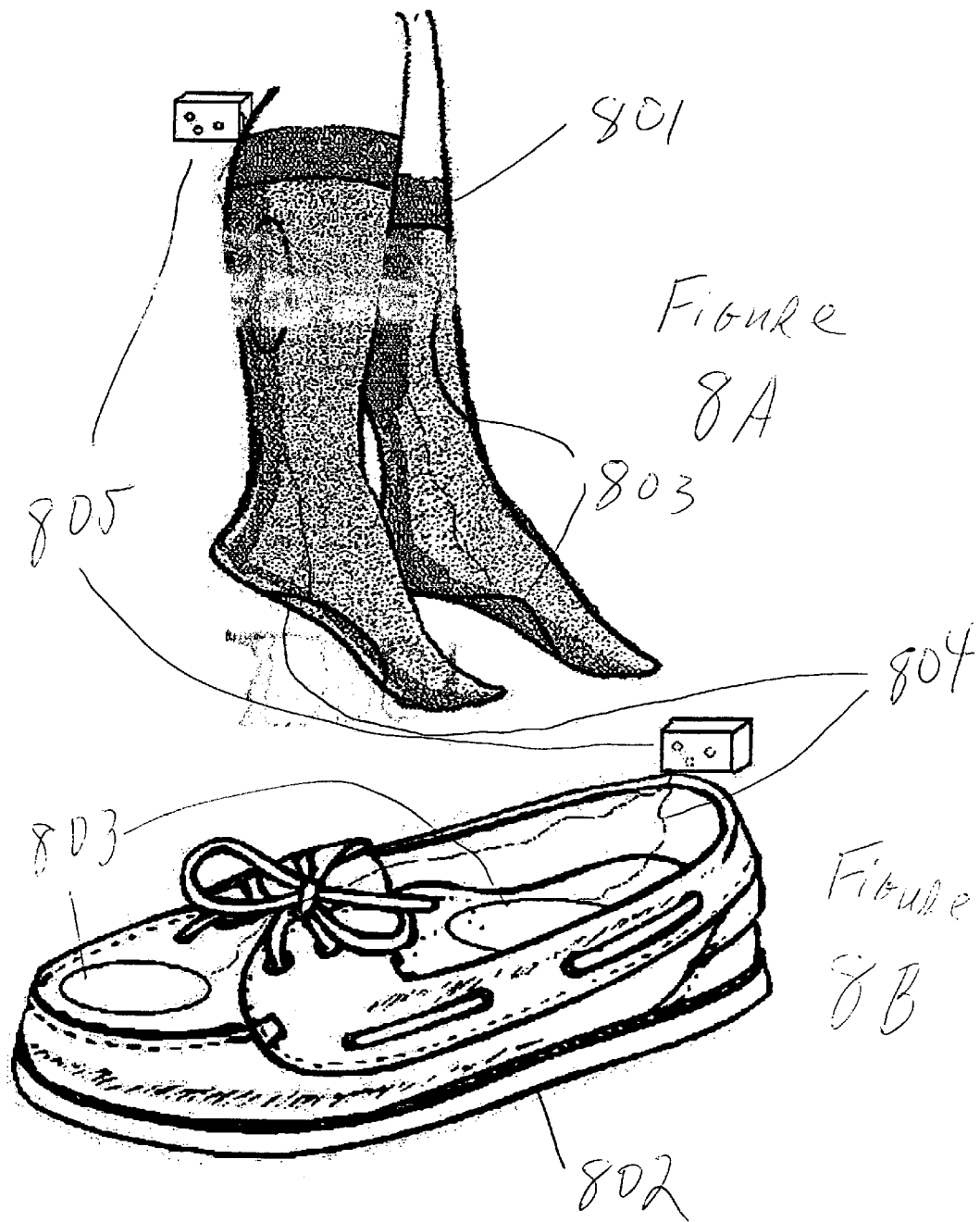
FIG. 8A depicts an electromagnetic treatment inductive apparatus integrated into a sock according to a preferred embodiment of the present invention.
FIG. 8B depicts an electromagnetic treatment inductive apparatus integrated into a shoe according to a preferred embodiment of the present invention.

Referring to FIGS. 8A and 8B an embodiment according to the present invention of an electromagnetic treatment inductive apparatus integrated into a sock 801 and a shoe 802 are illustrated. Several lightweight flexible coils 803 are integrated into the dressing. The lightweight flexible coils can be constructed from fine flexible conductive wire, conductive thread, and any other flexible conductive material. The flexible coils are connected to at least one end of at least one wire 804. However, the flexible coils can also be configured to be directly connected to circuitry 805 or wireless. Lightweight miniaturized circuitry 805 that configures waveforms according to an embodiment of the present invention, is attached to at least one other end of said at least on wire. When activated the lightweight miniaturized circuitry 805 configures waveforms that are directed to the flexible coils (806) to create PEMF signals that are coupled to a target pathway structure.

Figure 9:
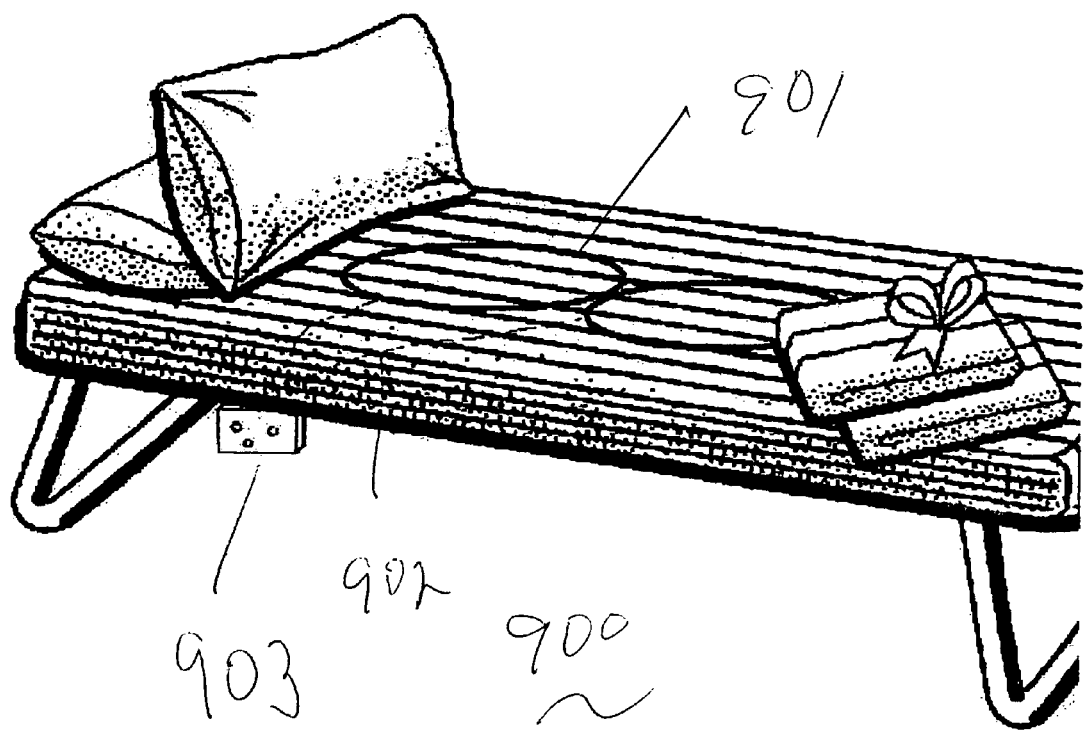
FIG. 9 depicts an electromagnetic treatment inductive apparatus integrated into a therapeutic bed according to a preferred embodiment of the present invention.

Referring to FIG. 9 an embodiment according to the present invention of an electromagnetic treatment inductive apparatus integrated into a therapeutic bed 900 is illustrated. Several lightweight flexible coils 901 are integrated into the bed. The lightweight flexible coils can be constructed from fine flexible conductive wire, conductive thread, and any other flexible conductive material. The flexible coils are connected to at least one end of at least one wire 902. However, the flexible coils can also be configured to be directly connected to circuitry 903 or wireless. Lightweight miniaturized circuitry 903 that configures waveforms according to an embodiment of the present invention, is attached to at least one other end of said at least on wire. When activated the lightweight miniaturized circuitry 903 configures waveforms that are directed to the flexible coils (901) to create PEMF signals that are coupled to a target pathway structure.

Figure 10:
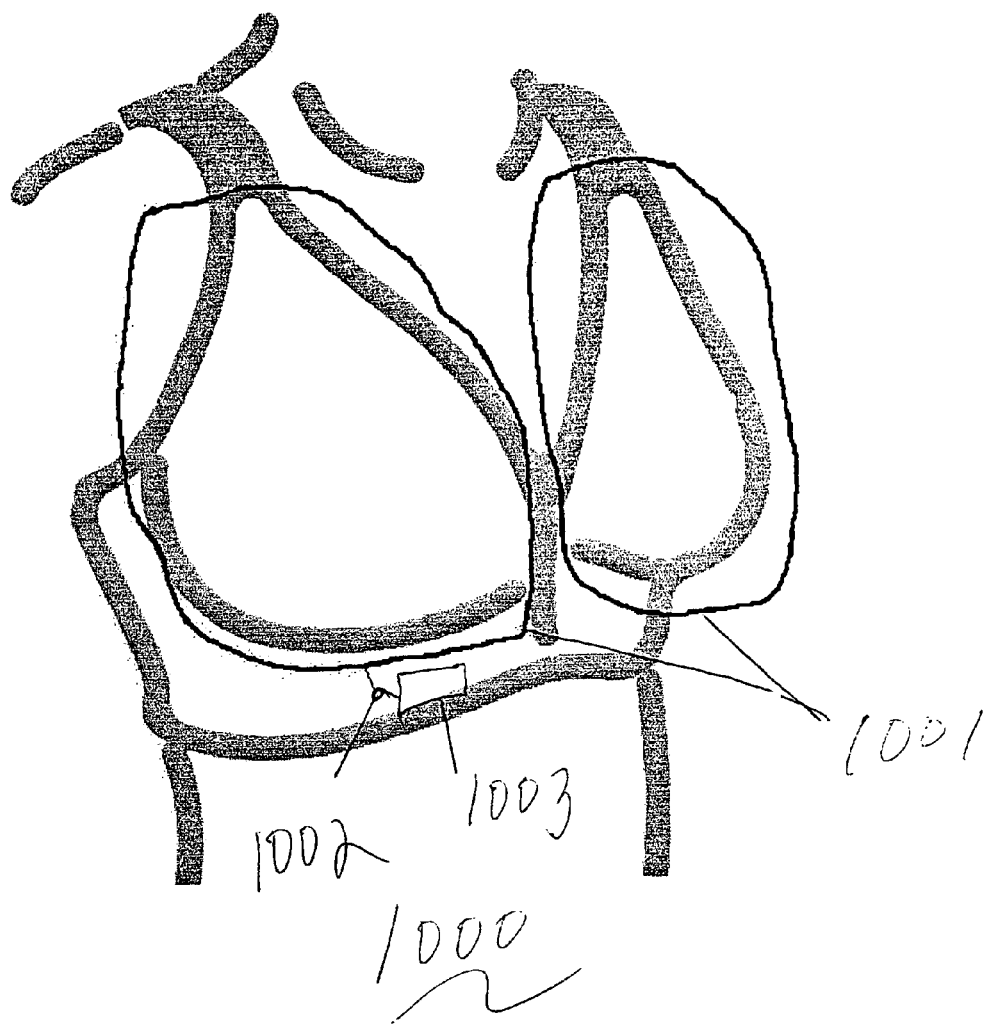
FIG. 10 depicts an electromagnetic treatment inductive apparatus integrated into a chest garment according to a preferred embodiment of the present invention.

Referring to FIG. 10 an embodiment according to the present invention of an electromagnetic treatment inductive apparatus integrated into a chest garment 1000, such as a bra is illustrated. Several lightweight flexible coils 1001 are integrated into a bra. The lightweight flexible coils can be constructed from fine flexible conductive wire, conductive thread, and any other flexible conductive material. The flexible coils are connected to at least one end of at least one wire 1002. However, the flexible coils can also be configured to be directly connected to circuitry 1003 or wireless. Lightweight miniaturized circuitry 1003 that configures waveforms according to an embodiment of the present invention, is attached to at least one other end of said at least on wire. When activated the lightweight miniaturized circuitry 1003 configures waveforms that are directed to the flexible coils (1001) to create PEMF signals that are coupled to a target pathway structure.

Having described embodiments for an electromagnetic treatment inductive apparatus and a method for using same, it is noted that modifications and variations can be made by persons skilled in the art in light of the above teachings. It is therefore to be understood that changes may be made in the particular embodiments of the invention disclosed which are within the scope and spirit of the invention as defined by the appended claims.

What is claimed is:

1. A method for using an electromagnetic treatment inductive apparatus comprising the steps of:
    Combining at least one inductive apparatus with a therapeutic device, wherein said therapeutic device is positioned in proximity to a target pathway structure;
    Configuring at least one waveform according to a mathematical model having at least one waveform parameter, said at least one waveform to be coupled to said target pathway structure;
    Choosing a value of said at least one waveform parameter to satisfy a signal to noise ratio model, so that said at least waveform is configured to be detectable in said target pathway structure above background activity in said target pathway structure;
    Generating an electromagnetic signal from said configured at least one waveform; and
    Coupling said electromagnetic signal to said target pathway structure using said at least one inductive apparatus device thereby providing treatment.

2. The method of claim 1, wherein said at least one waveform parameter includes at least one of a frequency component parameter that configures said at least one waveform to repeat between about 0.01 Hz and about 100 MHz, a burst amplitude envelope parameter that follows a mathematically defined amplitude function, a burst width parameter that varies at each repetition according to a mathematically defined width function, a peak induced electric field parameter varying between about 1 µV/cm and about 100 mV/cm in said target pathway structure according to a mathematically defined function, and a peak induced magnetic electric field parameter varying between about 1 µT and about 0.1 T in said target pathway structure according to a mathematically defined function.

3. The method of claim 2, wherein said defined amplitude function includes at least one of a 1/frequency function, a logarithmic function, a chaotic function, and an exponential function.

4. The method of claim 1, wherein said target pathway structure includes at least one of a molecule, a cell, a tissue, and an organ.

5. The method of claim 1, wherein said therapeutic device includes at least one of an anatomical supports, anatomical wraps, dressings, apparel, mattresses, a mattress pads, wheelchairs, therapeutic chairs, therapeutic beds, chairs, beds, cushions, and sporting goods.

6. The method of claim 5, wherein said apparel includes at least one of garments, fashion accessories, shoes, socks, and footware.

7. The method of claim 5, wherein said therapeutic device is portable.

8. The method of claim 5, wherein said therapeutic device is disposable.

9. The method of claim 5, wherein said therapeutic device is implantable.

10. The method of claim 1, further comprising the step of simultaneously generating said electromagnetic signal to a plurality of said at least one inductive apparatus.

11. The method of claim 10, wherein said Electromagnetic signal is generated from at least one of, identically configured said at least one waveforms, and differently configured said at least one waveforms.

12. The method of claim 1, further comprising the step of sequentially generating an electromagnetic signal to a plurality of said at least one inductive apparatus.

13. The method of claim 12, wherein said Electromagnetic signal is generated from at least one of, identically configured said at least one waveforms, and differently configured said at least one waveforms.

14. The method of claim 1, further comprising the step of multiplexing an electromagnetic signal to a plurality of said at least one inductive apparatus.

15. The method of claim 14, wherein said electromagnetic signal is generated from at least one of, identical at least one of said configured waveforms, and different at least one of said configured waveforms.

16. The method of claim 1, further comprising the step of using at least one of standard medical therapies and non-standard medical therapies adjunctively with said electromagnetic treatment inductive apparatus.

17. The method of claim 1, further comprising the step of using at least one of standard physical therapies and non-standard physical therapies conjunctively with said electromagnetic treatment inductive apparatus.

18. The method of claim 17, wherein standard physical therapies includes at least one of ultrasound, negative pressure, positive pressure, heat, cold, massage, exercise, and acupuncture.

19. The method of claim 1, further comprising the step of using said electromagnetic treatment inductive apparatus to modulate the production and utilization of growth factors, cytokines, and regulatory substances by living cells.

20. The method of claim 1, further comprising the step of using said electromagnetic treatment inductive apparatus to modulate tissue growth and repair.

21. The method of claim 1, further comprising the step of using said electromagnetic treatment inductive apparatus to reduce chronic and acute pain of musculoskeletal and neural origin.

22. The method of claim 1, further comprising the step of using said electromagnetic treatment inductive apparatus to reduce edema.

23. The method of claim 1, further comprising the step of using said electromagnetic treatment inductive apparatus for treatment of diabetic and pressure ulcers wherein said ulcers are chronic.

24. The method of claim 1, further comprising the step of using said electromagnetic treatment inductive apparatus for at least one of increasing blood flow and microvascular blood perfusion.

25. The method of claim 1, further comprising the step of using said electromagnetic treatment inductive apparatus for at least one of neovascularization and angiogenesis.

26. The method of claim 1, further comprising the step of using said electromagnetic treatment inductive apparatus to enhance immune response for malignant and benign conditions.

27. The method of claim 1, further comprising the step of using said electromagnetic treatment inductive apparatus to enhance transudation.

* * * * *